(12) United States Patent
Townsend

(10) Patent No.: US 7,779,547 B2
(45) Date of Patent: Aug. 24, 2010

(54) APPARATUS AND METHOD FOR SETTING FURNITURE HEIGHT

(76) Inventor: Robin Townsend, Skye (AU)

( * ) Notice: Subject to any disclaimer, the term of this patent is extended or adjusted under 35 U.S.C. 154(b) by 249 days.

(21) Appl. No.: 11/916,757

(22) PCT Filed: Jun. 6, 2005

(86) PCT No.: PCT/AU2005/000805
§ 371 (c)(1),
(2), (4) Date: Mar. 26, 2008

(87) PCT Pub. No.: WO2005/120296
PCT Pub. Date: Dec. 22, 2005

(65) Prior Publication Data
US 2008/0201970 A1    Aug. 28, 2008

(30) Foreign Application Priority Data
Jun. 7, 2004    (AU) ............................. 2004903016
Apr. 4, 2005    (AU) ............................. 2005901607

(51) Int. Cl.
*A61B 5/103*    (2006.01)
*G01B 3/02*    (2006.01)

(52) U.S. Cl. .............................. 33/494; 33/512
(58) Field of Classification Search ................ 33/494
See application file for complete search history.

(56) References Cited

U.S. PATENT DOCUMENTS

| | | | | | |
|---|---|---|---|---|---|
| 2,830,303 | A | * | 4/1958 | Sandock | 5/658 |
| 4,495,709 | A | * | 1/1985 | Mainenti | 33/484 |
| 4,728,150 | A | * | 3/1988 | Gaudreau, Jr. | 297/383 |
| 4,750,268 | A | * | 6/1988 | Ravid | 33/2 H |
| 4,894,600 | A | * | 1/1990 | Kearney | 318/649 |
| 4,942,670 | A | * | 7/1990 | Brandt | 33/494 |
| 5,060,896 | A | * | 10/1991 | Hobbins | 248/188.2 |
| 6,056,353 | A | * | 5/2000 | Meara | 297/41 |
| 6,145,210 | A | * | 11/2000 | Walczynski | 33/458 |
| RE37,212 | E | * | 6/2001 | Marshall | 33/759 |
| 7,249,423 | B2 | * | 7/2007 | Sieber | 33/512 |
| 2008/0216337 | A1 | * | 9/2008 | Chen | 33/759 |
| 2009/0126211 | A1 | * | 5/2009 | Mandaric | 33/503 |

FOREIGN PATENT DOCUMENTS

| | | |
|---|---|---|
| DE | 29803730 U1 | 5/1999 |
| DE | 20011279 U1 | 10/2000 |
| EP | 1106089 A2 | 6/2001 |

* cited by examiner

*Primary Examiner*—Christopher W Fulton
(74) *Attorney, Agent, or Firm*—The Webb Law Firm

(57) ABSTRACT

An apparatus for determining a desired height of a height adjustable furniture item, characterized in that it includes: a scale adapted to measure a length of the lower leg of a patient, means to determine a desired height of said item of furniture from said length and a means to translate said desired height to said furniture item.

12 Claims, 5 Drawing Sheets

APPARATUS AND METHOD FOR SETTING FURNITURE HEIGHT

FIELD OF THE INVENTION

The present invention relates to an apparatus and method for setting furniture height.

BACKGROUND OF THE INVENTION

The present invention relates to a method of quickly, simply and accurately adjusting furniture heights so that transfers (principally the sit-to-stand component) of principally aged, infirm or disabled people are facilitated. Mobility may be maximized, falls minimized and requirements for manual assistance reduced for this group of people.

It is acknowledged that 'sit to stand' transfers are amongst the most difficult for certain people, including the aged, infirm and disabled. These people frequently need considerable manual assistance from carriers to stand up from inappropriately adjusted seating, with shoulder and other musculo-skeletal injuries commonly resulting to nursing and care staff as well as patients. Falls may occur when inappropriately adjusted seating contributes to a poor sit-to-stand technique and poor initial standing balance. Falls that may be attributed to inappropriately adjusted seating are common amongst aged people, particularly within residential aged care facilities and hospitals, and may contribute to injuries to aged and disabled people.

Research and clinical experience show that if beds, chairs, shower chairs, toilet seat raisers, commodes and other similar items of furniture in use by persons of this type can be set to an appropriate height with particular respect to:

lower leg length of user/occupant
 strength of user/occupant
 balance ability of user/occupant.

By so doing, falls, injuries and associated inconvenience to patients and their support staff can be greatly reduced.

The present invention is directed to this need and provides an apparatus and method devices that can be used to minimise this currently widespread problem.

This invention is intended to enable accurate adjustment of appropriate furniture heights to enable their easier use by frail, aged, infirm or disabled people.

It is apparent from recent research and from the experience of clinicians that falls and balance problems, and the need for manual assistance, resulting in injuries to patients and/or care staff are greatly reduced if bed, chair, toilet raiser, commode, shower chair etc heights are correctly adjusted with respect to the lower leg length, strength, balance and frailty of the user.

Individual experienced clinicians are able to calculate appropriate heights and adjustments for the abovementioned, and other, items of furniture; however a general, simple method or system to enable appropriate adjustments to be made to those (and other) items of furniture by inexperienced or otherwise unqualified care staff, has been lacking.

SUMMARY OF THE INVENTION

Therefore according to the invention there is provided an apparatus for determining a desired height of a height adjustable furniture item, characterized in that it includes: a scale adapted measure a length of the lower leg of a patient, means to determine a desired height of said item of furniture from said length and a means to translate said desired height to said furniture item.

Preferably, said furniture item may be selected from a chair, a commode, a shower chair, a toilet raiser, a wheelchair, a mattress, or other seating.

Preferably, the desired height for said furniture item is 100-120% of the person's lower leg height.

Preferably, the scale groups lower leg lengths into a series of classifications and then relates these classifications mathematically to appropriate heights above floor level of the item of furniture, to thereby provide an indication of a height to which the furniture is to be adjusted.

Preferably, the desired height is translated to the item of furniture via an indicator tag. The indicator tag may be attached, as convenient, to a movable mattress support frame of an adjustable bed. The indicator tag enables the height above floor level of the upper surface of an adjustable bed to be rapidly set to the appropriate height.

In this form of the invention, indicator tag includes at the proximal end attachment means and adjustment means such that a cord can be attached or fixed to a bed frame of an adjustable bed and then the length of the cord and its attachments can be adjusted to and then held at a particular length as indicated by the scale and at the distal end a of appropriate size, permanently fixed to the cord.

In an alternative form of the invention the apparatus is generally rectangular in cross-section and has four separate faces Preferably, indicia used to measure a length of the lower leg of a patient are located on a separate face of said apparatus from indicia used to determine a desired height of said item of furniture from said leg length.

Preferably, indicia corresponding to different leg heights are, in use, made in different colours to facilitate ready identification and use.

Preferably, indicia used to determine a desired height of said item of furniture includes a vertical line indicating an acceptable height range wherein a the centre of the line representing the optimal point.

In one form of the invention an item of furniture is supplied an adjustable leg having attached thereto indicating a desirable adjustment height to accommodate a user of a particular leg length. The indicia may be a sticker having bands thereon, each band corresponding to a selected adjustment height.

In a still further form of the invention, height data for individual users may be recorded electronically and communicated electronically to furniture items for automatic height adjustment.

In a further form of the invention there is provided a method for determining a desired height of a height adjustable furniture item, characterized in that it includes the steps of.

measuring a length of the lower leg of a patient using a scale,
 determining a height classification for the patient from the scale
 establishing an adjustment height for the item of furniture from the scale.

DESCRIPTION OF DRAWINGS

The above and other objects, features, and advantages of the present invention will be apparent from the following detailed description of a preferred embodiment in conjunction with the accompanying drawings. In the drawings.

DESCRIPTION OF THE PREFERRED EMBODIMENT

Figure 1:
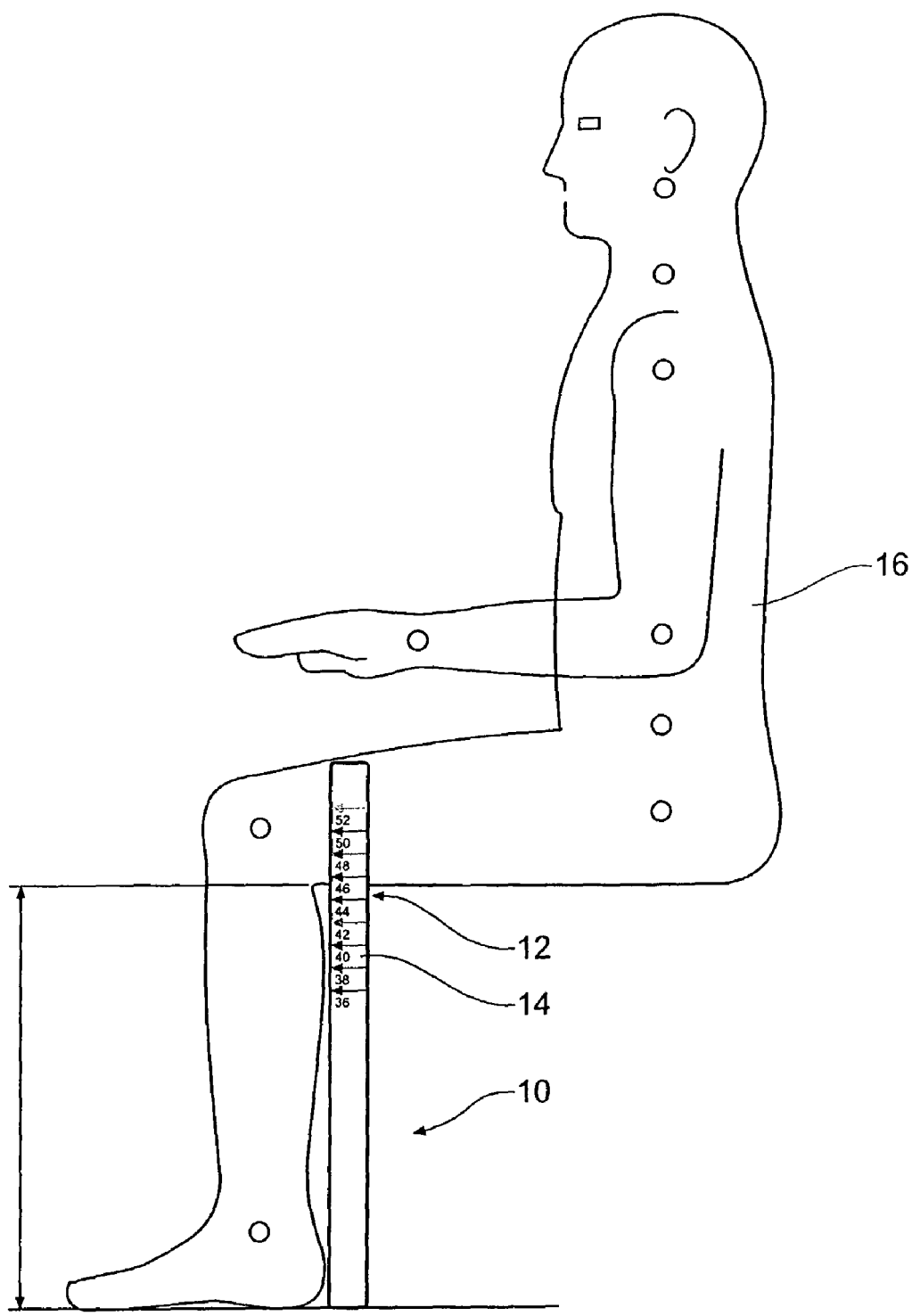
FIG. 1 illustrates a measuring device formed in accordance with a first aspect of the present invention in use.

Shown in the drawings are various embodiments incorporating a measuring device in accordance with the invention. The detailed description of the invention refers to the accompanying drawings. Although the description includes exemplary embodiments, other embodiments are possible, and changes may be made to the embodiments described without departing from the spirit and scope of the invention. Wherever possible, the same reference numbers will be used throughout the drawings and the following description to refer to the same and like parts.

Figure 2:
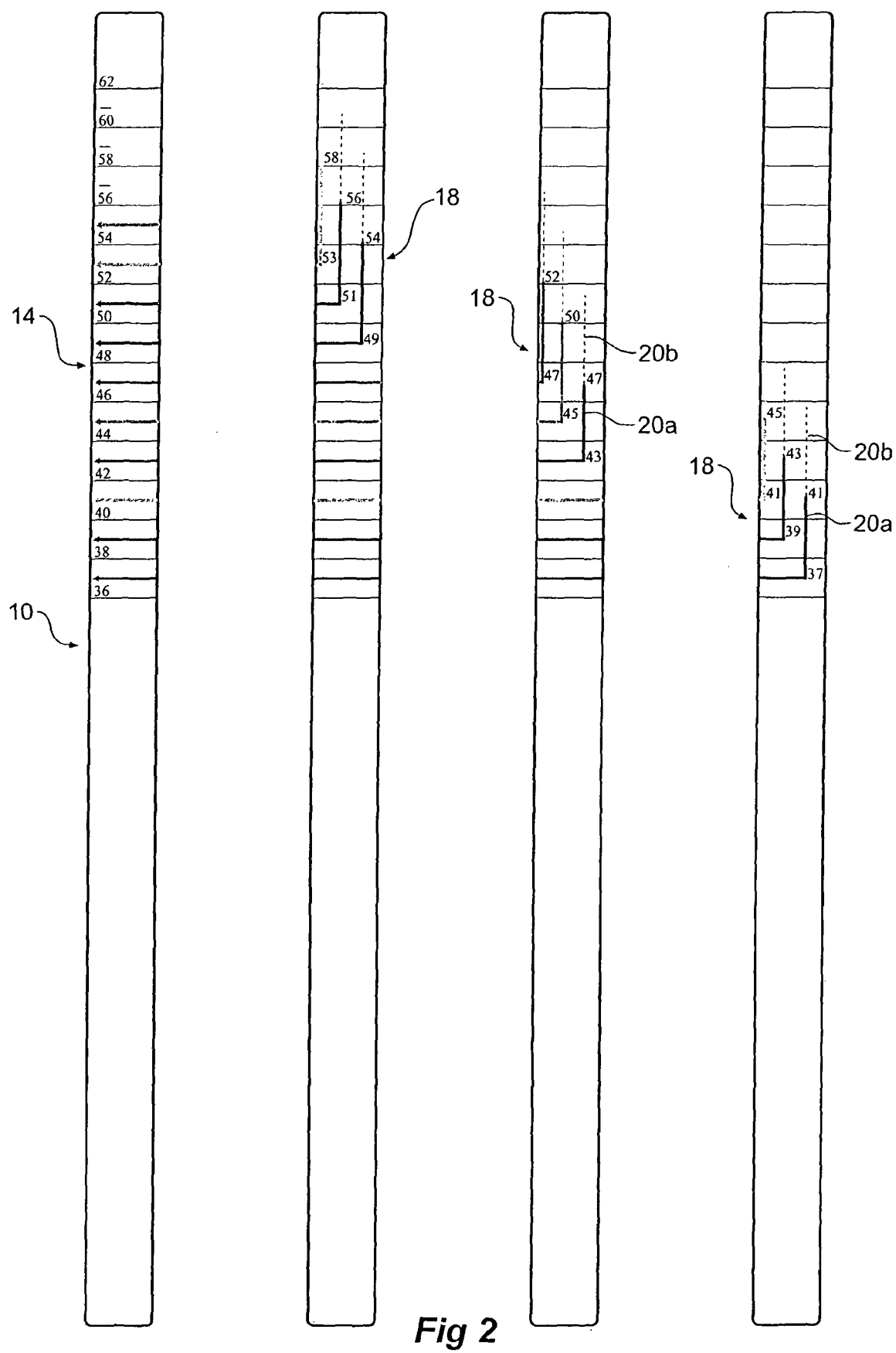
FIG. 2 shows the measuring device of FIG. 1 in greater detail.

Shown in FIGS. 1 and 2 is a measuring device 10 formed in accordance with the present invention. The measuring device 10 serves as an apparatus for determining a desired height of a height of a height adjustable furniture item (not shown). The device 10 includes a scale 12. The scale 12 includes indicia thereon, said indicia being both adapted measure a length 14 of the lower leg of a patient 16, and means 18 to determine a desired height of said item of furniture from said length and a means to translate said desired height to said furniture item (output). The device 10 is, in the embodiment illustrated generally rectangular in cross-section and has four separate faces as depicted in FIG. 2. Conveniently, the indicia that are used to measure the leg length 14, that is, the input are located on a separate side to the output information.

Specifically, the measuring device 10 includes thereon indicia, in the form of the scale 12, that represent the relationship and between a lower leg height and a desired height of the furniture item. The scale 12 consists of a series of marks that correspond to lower leg height and a vertical line 20 nomogram rising therefrom. The vertical line includes a lower half 20a drawn as solid and an upper half 20b shown as a dotted line. The vertical line 20 indicates the acceptable height of the furniture item for the corresponding leg height, with the centre of the line representing the optimal point.

To clarify matters, in use the various marks corresponding to different leg heights are, in use, made in different colours to facilitate ready identification and use. Thus, the device 10 is used as follows:

The device of the invention is thus predicated on the notion that an ideal height for a seat is 100-120% of the person's lower leg height as measured in FIG. 1. The information outputted from the device 10 is thus a reflection of this information 1. Persons lower leg length is measured using the scale, using the "input" edge of the scale, from floor to crease behind the knee. The person can thereby be sorted into a particular furniture height or colour classification;

2. By use of the nomogram section of the scale the proper range of heights for various items of furniture is determined. This can be done in one form of the invention by classifying the person (based on lower leg length) into one of a range of colours.

3. An assessment of the person's physical condition is made and this assessment used in conjunction with the nomogram section of the Scale to establish the particular suitable height (or where in the within the range encompassed by the colour) furniture should be set for the person in question 4. The height of the seats etc of most furniture items (with the exception of, inter alia, adjustable beds) can then be set by direct reference to the "output" or nomogram edge of the scale. This can be done by placing the Scale on the floor in the vertical position adjacent to the item of furniture whose appropriate height is to be set, and following the appropriate coloured line to the output edge and then adjusting the critical height of the furniture item so that its critical height matches the appropriate point within the "colour range" of the appropriate line.

Figure 3:
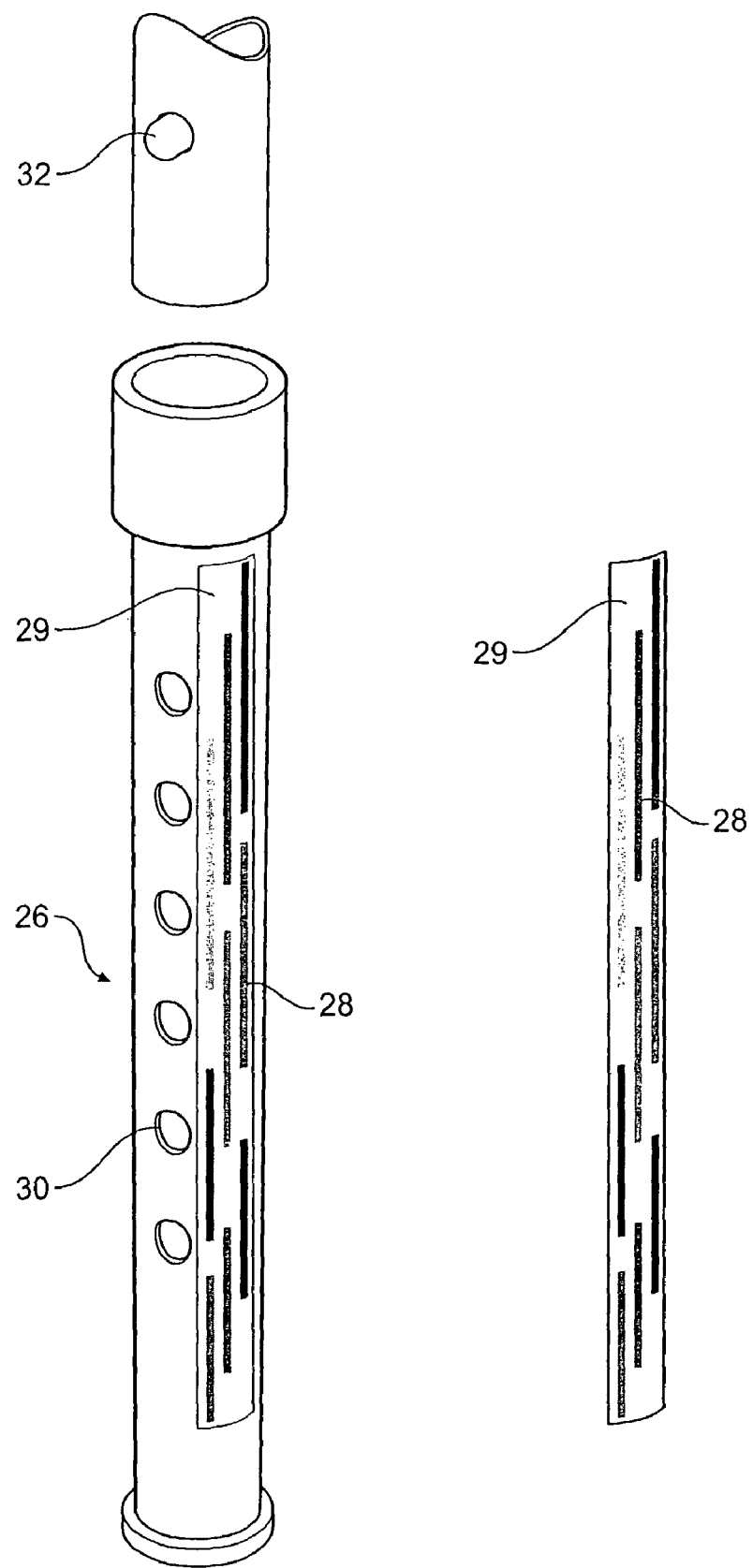
FIG. 3 below shows use of the measuring device as it may appear when incorporated as part of the design of adjustable furniture.
Figure 4:
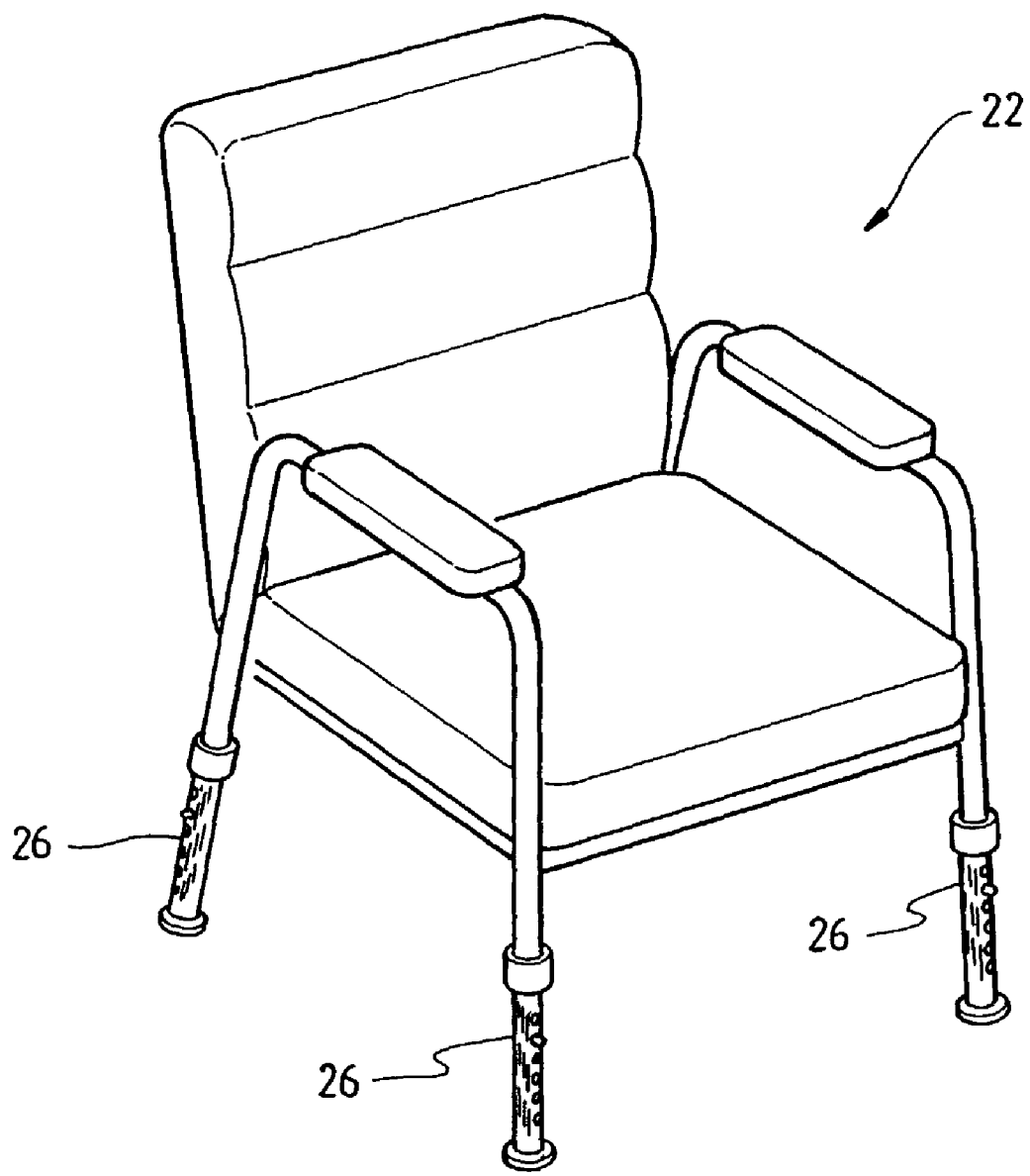
FIG. 4 illustrates the measuring device of the invention as incorporated into an adjustable chair.
Figure 5:
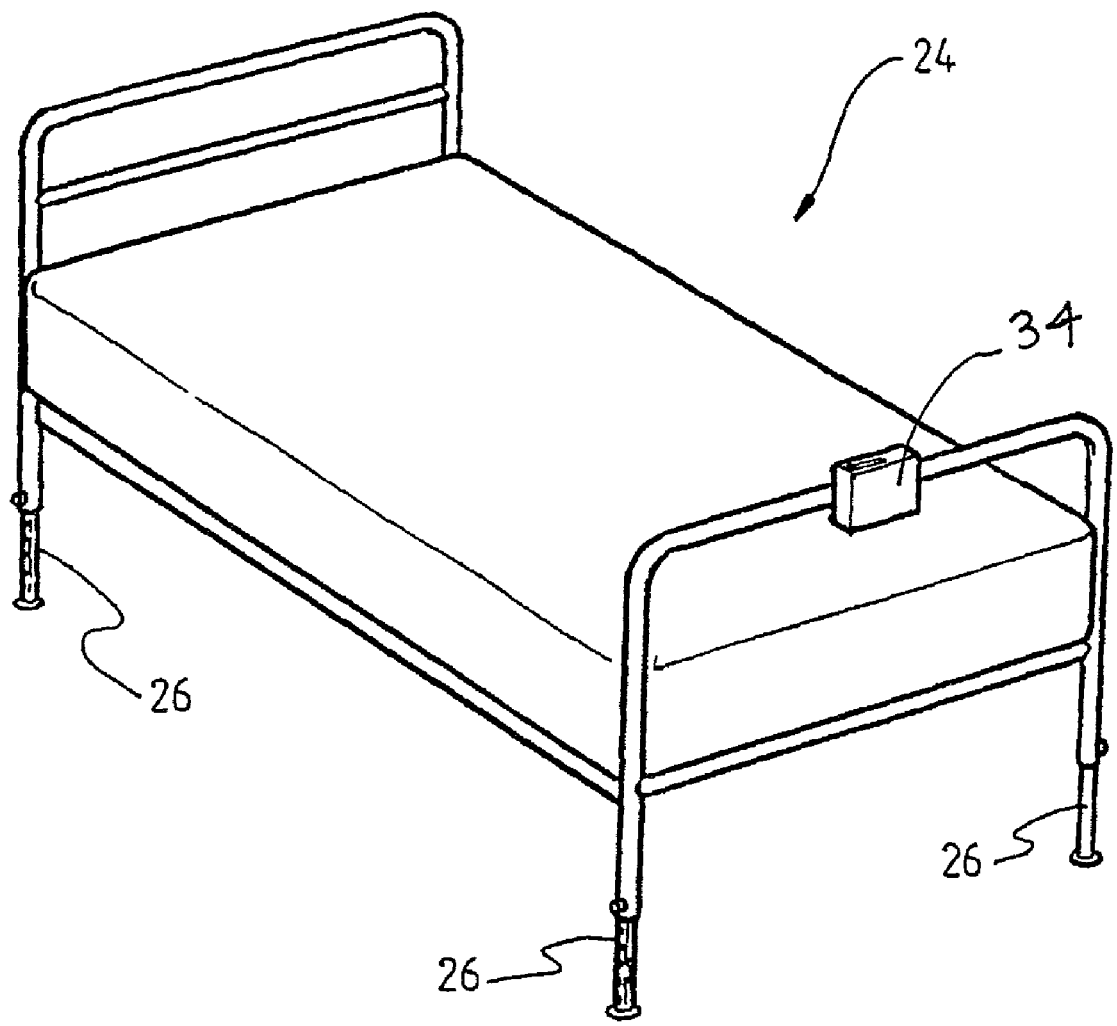
FIG. 5 illustrates the measuring device of the invention as incorporated into an adjustable bed.

Illustrated in FIGS. 4 and 5 are examples of a chair 22 and a bed 24 respectively. In each case the legs 26 of the item have attached thereto indicia in the form of a sticker 29 having coloured bands 28 thereon. A detail of a leg 26 is shown in FIG. 3. The leg 26 contains adjusting apertures 30 that act in cooperation with a biased stub 32. The bands 28 correspond to a height measured from the device 10 and thus tell a carer at what height the leg should be adjusted to accommodate a user of a particular leg length.

The measuring device of the invention may thus be used in the form of the device which can be carried by, and/or form part of the equipment of care staff and clinical professionals. The measuring device may adopt many forms (rigid, folding, telescopic etc) and those skilled in the art may be able to envisage still further forms and usages of the scale which will fall within the scope of the invention It will be appreciated that the measuring device does not require the specific item of furniture to be adjusted to bear the coloured bands 28. The output information from the device 10 may be simply in the form of a given height range. However, the use of corresponding coloured bands does simplify matters for the user.

In an alternative form of the invention, the measurements previously refereed to may be translated to a be or other seat by means of an indicator tag that consists of a length of inelastic cord of appropriate diameter or other material with:

- at the proximal end attachment means and adjustment means such that the cord can be attached or fixed to the bed frame of an adjustable bed and then the length of the cord and its attachments can be adjusted to and then held at a particular length as indicated by the Scale
- at the distal end a tag (of plastic material in the preferred embodiment) of appropriate size, permanently fixed to the cord.

The preferred method of operation of the indicator tag is as follows:

In the case of (inter alia) adjustable beds one method of using the invention could be:

a. classify the person's lower leg into one of the abovementioned classifications;

b. make assessment of the patient's physical condition;

c. read appropriate height range;

d. raised bed to a high height;

e. attach indicator tag firmly by its proximal attachment means to the moveable bed frame;

f. hold Scale so that the appropriate height indication is level with the upper surface of the mattress (after allowing for bodyweight compression when a person is seated on the side of the bed);

g. using the bed adjustment means set the length of indicator tag so that its distal end is level with the bottom of the scale; and h. progressively lower bed until the distal end of the tag just touches the floor.

Over lowering is easily detected as the tag "sags" out of the vertical, whilst a setting that is too high will be indicated by the tag not touching the floor.

A scale may be also attached to, stuck to, painted on etc to furniture, thus forming a system for the appropriate management of furniture heights for the frail, elderly, disabled or convalescent. In one form of the invention this would work as follows:

a. the "subject" is seated, foot flat on the floor and "measured" (lower leg length from floor to crease behind knee) with the Scale;

b. the subject is classified, based on the above measurement, plus assessment of strength balance and general physical condition, into one of the colour groups of the nomogram or Scale;

c. this classification is recorded in the subject's records; and d. furniture used by the subject can then be adjusted without further measurement by use of the Scale incorporated into the adjustable furniture. For example, if a subject is classified in the upper range of "red" then furniture to be used by the subject is adjusted, using the adjustment means designed into the adjustable item of furniture, such that its height corresponds to the upper range of "red.

In a still further form of the invention the subject or patient's classification could be recorded as data on a "smart card", bracelet or other data storage means carried or worn by the patient. This classification could then be "read" by smart furniture-, including beds, commodes, chairs and shower chairs which could then set themselves to the appropriate, programmed height, indicate that they were incorrectly adjusted or respond in some other way to achieve the correct setting. FIG. 5 includes a smart reader 34 attached thereto.

General method for using such a system is therefore a. Use scale to measure and classify subject;

b. record subject's classification; and c. set all appropriate furniture to the appropriate setting using scale or using scale incorporated into item of furniture as part of the system Further advantages and improvements may very well be made to the present invention without deviating from its scope. Although the invention has been shown and described in what is conceived to be the most practical and preferred embodiment, it is recognized that departures may be made therefrom within the scope and spirit of the invention, which is not to be limited to the details disclosed herein but is to be accorded the full scope of the claims so as to embrace any and all equivalent devices and apparatus.

The invention claimed is:

1. An apparatus for determining a desired height of a height adjustable furniture item, comprising:
a scale adapted measure a length of the lower leg of a patient;
means to determine a desired height of said item of furniture from said length; and
means to translate said desired height to said furniture item,
wherein the scale includes thereon indicia that represent the relationship between a lower leg height and a desired height of the furniture item, and
wherein the scale groups lower leg lengths into a series of classifications and then relates these classifications mathematically to appropriate heights above floor level of the item of furniture, to thereby provide an indication of a height to which the furniture is to be adjusted.

2. The apparatus according to claim 1, wherein the desired height for said furniture item is 100-120% of the person's lower leg height.

3. The apparatus according to claim 1, wherein said desired height is translated to the item of furniture via an indicator tag.

4. The apparatus according to claim 3, wherein the indicator tag is attached to a movable mattress support frame of an adjustable bed.

5. The apparatus according to claim 3, wherein the indicator tag enables the height above floor level of the upper surface of an adjustable bed to be rapidly set to the appropriate height.

6. The apparatus according to claim 1, wherein said apparatus is generally rectangular in cross-section and has four separate faces.

7. The apparatus according to claim 6, further including indicia, used to measure a length of the lower leg of a patient, located on a separate face of said apparatus from indicia used to determine a desired height of said item of furniture from said leg length.

8. The apparatus according to claim 6, further including indicia corresponding to different leg heights and made in different colours to facilitate ready identification and use.

9. The apparatus according to claim 1, further comprising indicia attachable to an adjustable leg of the item of furniture indicating a desirable adjustment height to accommodate a user of a particular leg length.

10. The apparatus according to claim 9, wherein said indicia is a sticker having bands thereon, each band corresponding to a selected adjustment height.

11. An apparatus for determining a desired height of a height adjustable furniture item, comprising:
a scale adapted measure a length of the lower leg of a patient;
means to determine a desired height of said item of furniture from said length;
means to translate said desired height to said furniture item; and
indicia used to determine a desired height of said item of furniture which includes a vertical line indicating an acceptable height range wherein a center of the line represents an optimal point,
wherein the scale includes thereon indicia that represent the relationship between a lower leg height and a desired height of the furniture item, and wherein said apparatus is generally rectangular in cross-section and has four separate faces.

12. An apparatus for determining a desired height of a height adjustable furniture item, comprising:
a scale adapted measure a length of the lower leg of a patient;
means to determine a desired height of said item of furniture from said length;
means to translate said desired height to said furniture item; and
indicia attachable to an adjustable leg of the item of furniture indicating a desirable adjustment height to accommodate a user of a particular leg length,
wherein the scale includes thereon indicia that represent the relationship between a lower leg height and a desired height of the furniture item, and wherein height data for individual users may be recorded electronically and communicated electronically to furniture items for automatic height adjustment.

* * * * *

UNITED STATES PATENT AND TRADEMARK OFFICE
CERTIFICATE OF CORRECTION

PATENT NO. : 7,779,547 B2  
APPLICATION NO. : 11/916757  
DATED : August 24, 2010  
INVENTOR(S) : Townsend Page 1 of 1

It is certified that error appears in the above-identified patent and that said Letters Patent is hereby corrected as shown below:

Column 5, line 49, Claim 1, "a scale adapted measure" should read
-- a scale adapted to measure --

Column 6, line 31, Claim 11, "a scale adapted measure" should read
-- a scale adapted to measure --

Column 6, line 48, Claim 12, "a scale adapted measure" should read
-- a scale adapted to measure --

Signed and Sealed this
Fourth Day of January, 2011

David J. Kappos
*Director of the United States Patent and Trademark Office*